United States Patent [19]

Carrier

[11] Plant 5,175

[45] Jan. 10, 1984

[54] CARNATION PLANT

[76] Inventor: Leonard E. Carrier, 1911 Sheridan Rd., Encinitas, Calif. 92024

[21] Appl. No.: 431,835

[22] Filed: Sep. 30, 1982

[51] Int. Cl.[3] ..... A01H 5/00
[52] U.S. Cl. ..... Plt./71
[58] Field of Search ..... Plt./71

*Primary Examiner*—Robert E. Bagwill
*Attorney, Agent, or Firm*—James R. Cypher

[57] ABSTRACT

The present invention relates to a new and distinct cultivar of carnation plant named Melody, which was originated by me by crossing numbered but unnamed and unpatented seedlings and from irradiation of a seedling derived from this cross.

1 Drawing Figure

SUMMARY OF THE DISCLOSURE

The present invention relates to a new and distinct cultivar of carnation plant which was originated by me in my commercial nursery at Encinitas, Calif. by cross-breeding numbered but unnamed and unpatented seedlings and irradiation of a seedling derived from this cross.

The primary objectives of this breeding were to produce an improved carnation cultivar having improved disease resistance and production qualities, along with improved flower color, size and form, as well as less tendency of the calyx to burst and cause "splits" as the flowers open fully, which is so typical of the species botanically known as *Dianthus caryophyllus.* These objectives were fully achieved, along with other desirable improvements, as evidenced by the following unique combination of principal characteristics which are outstanding in my new cultivar, Melody and which distinguish it from its parents, as well as from all other carnations of which I am aware:

1. A very vigorous and free-breaking plant habit with strong and straight stems;
2. Superior resistance to soil-borne diseases such as Fusarium oxysporium and Fusarium roseum and other root-rots such as damping off, water molds, and the like.
3. Large pink serrated flowers which open fully without bursting the calyx and causing "splits";
4. A distinctive and attractive pink flower color which fades to a slightly lighter shade at the margin, producing a frosted appearance.

Asexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

DRAWING

The accompanying drawing illustrates typical specimens of the vegetative growth and flowers of my new carnation in different stages of development and is depicted in color as nearly true as it is reasonably possible to make the same in a color illustration of this character.

DETAILED DESCRIPTION

The following is a detailed description of my new carnation cultivar, Melody with color terminology in accordance with Robert Ridgway's Color Standards and Nomenclature (1912 edition), except where general color terms of ordinary dictionary significance are obvious.

PLANT

Botanical classification: *Dianthus caryophyllus.*

Breeding: Seedling.

*Female parent.*—Numbered but unnamed and unpatented seedling.

*Male parent.*—Numbered but unnamed and unpatented seedling.

Form: Erect but free-branching.

Growth: Strong, heavy growth, stiff stems, and heavy waxy leaves.

Classification: Greenhouse type, suitable for cut flower production as a standard (one bloom per stem).

Propagation: Holds its distinguishing characteristics through succeeding propagations by rooted cuttings.

Locality where grown and observed: Encinitas, Calif.

Disease resistance: The new cultivar has shown no evidence of fusariums or other root rots, as determined by extensive tests in high infested soils inoculated with as many strains of fungi as are locally available in the area of Encinitas, Calif.; tests conducted without chemical or steam sterilization of the soil. Soils in which the carnation plant "Sim" and others soon die.

Temperature tolerance: Not hardy to cold, but grows best at temperature above 10° C.; has good resistance to hot weather in summer months of August and September at Encinitas, Calif., without hardening of growth and with only little reduction of flower size and little flower fading; no marked fading of outer flower petals even when bloom is past maturity.

Blooming period: Blooms under both long and short photoperiods.

Bud: Lobes of calyx overlap in tight bud and seldom split.

*Length.*—2.2 cm.

*Diameter.*—2.3 cm.

*Color.*—Deep Rose Pink, Plate XII, 71′ V-RR.

Peduncle:

*Strength.*—Strong.

*Color.*—Nickel Green, Plate XXXIII, 37′ GB-G.

Bloom:

*Size.*—7.5 to 8.0 cm. diameter, depth 3.0 cm.

*Stem.*—Consist of 9 nodes: Length is 50 cm. Diameter is 0.75 cm. at base and about 0.3 cm. at base of calyx. Color is Nickel Green, Plate XXXIII, 37′ GB-G.

*Petalage.*—From 90 to 100 petals. Outer petals are about 3.5 cm. wide and about 4.5 cm. long. Center petals are about 2.5 cm. wide and about 4.5 cm. long.

*Color.*—The center of flower, outer petals, base of petals, and inside of petals are all Deep Rose Pink (Plate XII, 71′ V-RR). Back of petals and margins are Thulite Pink, Plate XXVI, 71′ V-RR.

*General tonality.*—Medium pink bloom which has lighter pink on back of petals especially at the serration which gives it a frosted appearance.

*Petals.*—Texture is firm. Form: Outer petals nearly semi-circular, with shallow irregular serration (4 to a cm.). Opening: Normal with minimum of split calyx's.

*Fragrance.*—No distinctive fragrance.

Foliage:

*Form.*—Concave.

*Size.*—1.2 cm. wide and 13 cm. long.

*Quantity.*—Two leaves per node, with nodes spaced about 8 cm. apart.

*Color.*—The upper and under sides of both young and mature plants are all Nickel Green, Plate XXXIII, 37′ GB-G.

*Texture.*—Smooth.

I claim:

1. A new and distinct cultivar of carnation plant named Melody substantially as herein shown and described, characterized particularly as to novelty by the unique combination of a very vigorous and free-breaking plant habit, and strong and straight stems; superior resistance to soil-borne diseases such as Fusarium oxysporium and Fusarium roseum and other root-rots such as damping off, water molds, and the like; large serrated flowers which open fully without bursting the calyx and causing "splits"; a distinctive and attractive pink flower color which fades evenly to a slightly lighter shade of pink giving a frosted appearance; and good heat tolerance which is superior to that of the parent lines and the so-called "Sim".

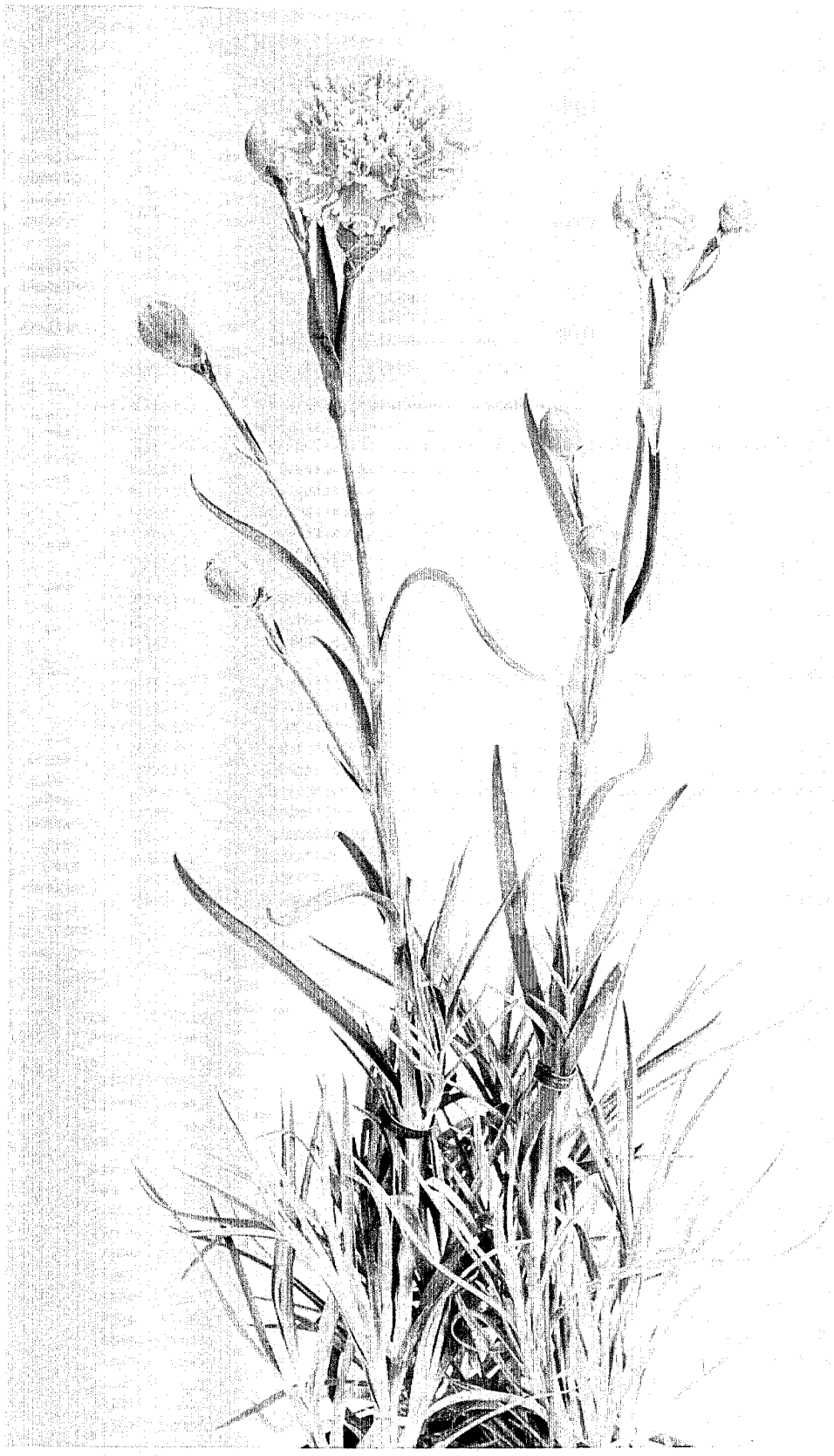

* * * * *